United States Patent [19]

Merkel et al.

[11] Patent Number: 4,700,000

[45] Date of Patent: Oct. 13, 1987

[54] PREPARATION OF CALCIUM PROPIONATE

[75] Inventors: Dieter Merkel, Ludwigshafen; Wolfgang Muehlthaler, Hemsbach; Hans Diem, Mannheim; Guenther Matthias, Frankenthal, all of Fed. Rep. of Germany

[73] Assignee: BASF Aktiengesellschaft, Fed. Rep. of Germany

[21] Appl. No.: 691,373

[22] Filed: Jan. 14, 1985

Related U.S. Application Data

[63] Continuation of Ser. No. 489,011, Apr. 27, 1983.

[30] Foreign Application Priority Data

Apr. 28, 1982 [DE] Fed. Rep. of Germany ....... 3215752

[51] Int. Cl.$^4$ ............................................. C07C 51/41
[52] U.S. Cl. .................................................... 562/606
[58] Field of Search ......................................... 562/606

[56] References Cited

U.S. PATENT DOCUMENTS 2,898,372 8/1959 Anderson ............................ 562/606

FOREIGN PATENT DOCUMENTS 1217381 4/1963 Fed. Rep. of Germany .
684155 10/1952 United Kingdom .

OTHER PUBLICATIONS

Levenspiel, O., *Chemical Reaction Engineering*, 2nd Ed., Wiley, New York, 1972, p. 409.
Glasstone, S., *Physical Chemistry*, 2nd ed., MacMillan and Co., London (1962), pp. 1111-1112.
Denbigh, K., *Chemical Reactor Theory*, Cambridge University Press, Cambridge, (1966), pp. 12-13, 27-28.

*Primary Examiner*—Donald B. Moyer
*Assistant Examiner*—Bruce D. Gray
*Attorney, Agent, or Firm*—Keil & Weinkauf

[57] ABSTRACT

Calcium propionate is prepared by passing a vaporous mixture of propionic acid and water into an aqueous solution containing calcium propionate and calcium hydroxide, with or without propionic acid.

4 Claims, No Drawings

PREPARATION OF CALCIUM PROPIONATE

This application is a continuation of application Ser. No. 489,011, filed on Apr. 27,1983.

The present invention relates to a novel process for the preparation of calcium propionate.

This compound is used on a large scale as a preservative in the foodstuffs sector and in the storage of animal feeds (K. WEISSERMEL and H. J. ARPE "Industrielle organische Chemie", page 115, Verlag Chemie 1976) and is prepared by the conventional methods for synthesizing carboxylic acid salts, for example by reacting a carbonate, hydroxide or oxide with a concentrated or dilute carboxylic acid.

The reaction of calcium hydroxide with propionic acid proceeds exothermically, in accordance with the following equation:

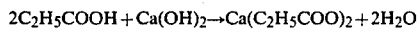

$$2C_2H_5COOH + Ca(OH)_2 \rightarrow Ca(C_2H_5COO)_2 + 2H_2O$$

The heat of reaction can be removed partly by heat transfer to additional auxiliaries and partly by evaporation of the water.

Japanese Pat. No. 14684/1968 proposes fine grinding of propionic acid and calcium hydroxide with water to form a paste. Addition of dry calcium propionate gives a doughy substance, which is dried.

British Pat. No. 684,155 discloses another possibility, which comprises reacting calcium oxide or hydroxide with propionic acid in the presence of a polyhydric alcohol, e.g. glycol. The reaction can also be carried out in the presence of solid, inert foreign substances. Thus, German Patent Application No. P 53 194 D discloses the reaction of concentrated propionic acid with a metal oxide or carbonate in the presence of soybean flour or malt flour.

Finely divided inert inorganic substances, e.g. kieselguhr or talc, can also be thoroughly mixed with the reactants. In order to increase the rate of the reaction, the process is carried out in a warm stream of air, if required, in a moving bed or fluidized bed (German Pat. No. 1,217,381).

However, inert auxiliaries cannot be used if, as in the present case, pure calcium propionate is to be prepared. Under these circumstances, it is advantageous to utilize the heat of reaction in a controlled manner for evaporating the water formed.

439 kJ are required to evaporate the 0.194 kg of water simultaneously formed with 1 kg of calcium propionate. The 670 kJ of heat liberated per kg of calcium propionate are therefore sufficient.

However, since all the reactants, i.e. propionic acid, calcium hydroxide, calcium propionate and water, are always in the reactor at the same time in the case of the continuous procedure, an azeotropic mixture containing about 75% by weight of water and about 25% by weight of propionic acid is evaporated instead of pure water. There is thus the problem of finding a suitable way of utilizing this vaporous mixture of propionic acid and water continuously obtained.

If the vaporous mixture is condensed and the condensate is recycled to the reactor, the water content in the reactor increases, whereupon the consistency of the reaction mixture changes. Instead of granular calcium propionate, a sludgy product is obtained.

It is very expensive to work up the condensate by distillation. In addition, any impurities which the propionic acid may contain and which cannot be removed by distillation become more concentrated.

The reaction of the condensed vaporous mixture with calcium hydroxide is also unsuitable, because extensive energy-consuming drying processes, e.g. spray-drying, are necessary because of the high water content.

We have found that a vaporous mixture containing from 20 to 30% by weight of propionic acid and from 70 to 80% by weight of water can advantageously be used for the preparation of calcium propionate by a process wherein this mixture is passed into an aqueous mixture containing calcium propionate and calcium hydroxide, with or without propionic acid, during which the pH is brought to 5-10 by further addition of calcium hydroxide, and the calcium propionate is isolated by crystallization.

Specifically, the process according to the invention is carried out, for example, as follows:

A vaporous mixture of propionic acid and water having a composition corresponding to that of the azeotrope escapes from a continuously operated reactor A, in which propionic acid is reacted with calcium hydroxide. This vaporous mixture generally contains from 10 to 300% by weight of inert gas, preferably nitrogen, based on the vaporous mixture of propionic acid and water.

The composition of an azeotropic mixture depends to a small extent on the pressure. In the present case, the components of the pressure are the partial pressures of the propionic acid vapor, the steam and the inert gas, and the pressure varies within the range from 0.5 to 20 bar. The composition of the azeotrope can thus vary between the above limits.

The vaporous mixture is heated to 90°-165° C. by the heat of reaction liberated in reactor A and by means of additional heating, and is passed into a reactor B.

Reactor B can be operated in two different temperature ranges. A distinction into two temperature ranges is appropriate, because the preparation process provides for two different, temperature-dependent methods of working up which give different purities of calcium propionate. The choice of temperature range thus depends on the desired quality of the calcium propionate.

If reactor B is operated in the lower temperature range, the vaporous mixture is passed in continuously under a pressure of from 0.5 to 2 bar. An aqueous mixture containing from 27 to 50% by weight of calcium propionate, from 0.1 to 5% by weight of calcium hydroxide and from 0.005 to 1% by weight of propionic acid is stirred in reactor B at from 70° to 120° C., preferably from 80° to 100° C. Of the calcium propionate, 27% by weight is in solution and the remainder is in the form of a solid monohydrate. Of the calcium hydroxide, about 0.05% by weight is in solution and the remainder is present as a solid. The pH of the mixture is from 5 to 10, preferably from 8 to 9.

The aqueous mixture flows continuously through reactor B. Its residence time in the reactor is from 0.1 to 2 hours, preferably from 0.2 to 0.5 hour. A vaporous mixture containing $\leq 0.1\%$ of propionic acid escapes from the reactor.

The reactor product, which contains dissolved calcium propionate and solid calcium propionate monohydrate, is separated into its components in a conventional manner, for example by filtration, decantation or centrifugation. The solid is then dried and ground in a conventional manner, while the solution, which contains not less than 27% by weight of calcium propionate, is recycled continuously into reactor B.

The space/time yield of calcium propionate monohydrate is from 0.1 to 1 kg per hour, based on a reactor volume of 1 liter.

The calcium hydroxide used in the reaction usually contains heavy metal salts, chiefly iron salts. In order to obtain a highly pure end product which is free from heavy metals, the calcium propionate must be dissolved completely so that the insoluble heavy metal hydroxides can be removed.

This is advantageously achieved with a saturated solution of calcium propionate. However, since calcium propionate has a solubility minimum at 55° C., it is necessary to heat the mixture to far above 100° C. and to produce a saturated solution at about 200° C. in order thus to obtain a high concentration gradient. Reactor B is operated in the upper temperature range to produce a saturated calcium propionate solution. The vaporous mixture is compressed to a pressure of from 2 to 20 bar and is passed continuously into reactor B, in which an aqueous mixture containing from 27 to 80% by weight of dissolved calcium propionate, from 0.1 to 5% by weight of calcium hydroxide and from 0.005 to 1% by weight of propionic acid is stirred at from 120° to 210° C. The calcium propionate is thereby completely dissolved, while calcium hydroxide is partly in solution and partly present as a solid.

In this case also, the aqueous mixture flows continuously through reactor B, its residence time corresponding to the above values. A vaporous mixture containing ≦0.1% of propionic acid escapes from the reactor.

The reactor product, which contains dissolved calcium propionate and insoluble heavy metal hydroxides, is filtered at from 120° to 210° C. corresponding to a vapor pressure of from 2 to 20 bar to remove the impurities. The filtrate is then cooled to 30°-80° C., whereupon calcium propionate monohydrate precipitates. This is separated off as described above and dried and ground in a conventional manner, while the solution, which contains not less than 27% by weight of calcium propionate, is recycled continuously to reactor B.

The novel process according to the invention enables the vaporous azeotropic mixture of propionic acid and water continuously obtained in a continuous process for the preparation of calcium propionate to be used directly again, without intermediate condensation, for the preparation of calcium propionate in a parallel process which is likewise operated continuously.

Complete conversion is thereby achieved in a three-phase reaction at a high reactor throughput and a very low concentration of both dissolved calcium hydroxide and propionic acid.

In the Examples which follow and which illustrate the process according to the invention, percentages are by weight.

EXAMPLE 1

7,237.4 parts per hour of a vaporous mixture containing 25% of propionic acid, 75% of water and 126% of nitrogen, based on the vaporous mixture of propionic acid and water, were passed continuously into a stainless steel absorption reactor, equipped with a stirrer, into which 5,096 parts per hour of an aqueous solution containing 27% of calcium propionate were introduced continuously. The vaporous mixture was at 138° C. and under a pressure of 1.05 bar.

400 parts per hour of calcium hydroxide were also added continuously, via a screw conveyor, in a manner such that the pH of the mixture was 8.

The temperature of the mixture was 98° C. and its average residence time in the reactor was 0.5 hour. A vaporous mixture containing ≦0.1% of propionic acid escaped from the reactor.

6,257 parts per hour of the mash in the reactor were continuously discharged and were separated into its components in a centrifuge. 1,211 parts per hour of a free-flowing solid containing 83% of calcium propionate and 17% of water were thereby obtained. The solid was dried until its water content had dropped to about 1%, and was then ground. 5,096 parts per hour of an aqueous solution containing 27% of calcium propionate were obtained as the centrifugate and were recycled continuously to the reactor.

EXAMPLE 2

7,235.9 parts per hour of a vaporous mixture containing 25% of propionic acid, 75% of water and 126% of nitrogen, based on the vaporous mixture of propionic acid and water, were passed continuously into a stainless steel absorption reactor, equipped with a stirrer, into which 2,455 parts per hour of a suspension containing 400 parts of calcium hydroxide and 2,055 parts of a 27% strength aqueous calcium propionate solution were introduced continuously. The vaporous mixture was at 147° C. under a pressure of 1.05 bar.

Before the vaporous mixture entered the reactor, its pressure was increased to 10.2 bar to overcome the counterpressure of the reactor.

The temperature of the reaction mixture was 180° C. and its average residence time in the reactor was 0.5 hour. A vaporous mixture containing ≦0.1% of propionic acid escaped from the reactor.

3,063 parts per hour of the suspension in the reactor were removed continuously and filtered, a filter residue of one part of hydrated iron oxide being obtained. The filtrate was cooled to 55° C., and 1,005.5 parts per hour of calcium propionate thereby precipitated as a crystalline residue. After letting down to normal pressure, the mixture was separated into its components in a centrifuge. 1,211 parts per hour of a highly pure free-flowing solid containing 83% of calcium propionate and 17% of water were obtained. The solid was dried until its water content had dropped to about 1% and was then ground.

2,055 parts per hour of an aqueous solution containing 27% of calcium propionate were obtained as the centrifugate. 400 parts per hour of calcium hydroxide were added and the mixture was recycled continuously to the reactor.

We claim:

1. A process for the preparation of calcium propionate starting from calcium hydroxide and propionic acid, wherein in a three-phase reaction a vaporous mixture containing from 20 to 30% by weight of propionic acid and from 70 to 80% by weight of water is passed into an aqueous mixture containing calcium propionate and calcium hydroxide, with or without propionic acid, during which the pH is brought to 5-10 by further addition of calcium hydroxide, and the calcium propionate is isolated by crystallization.

2. A process as claimed in claim 1, wherein the vaporous mixture, which is at from 90° to 165° C. under a pressure of from 0.5 to 2 bar, is passed into an aqueous mixture, at from 70° to 120° C., containing from 27 to 50% by weight of calcium propionate, from 0.1 to 5% by weight of calcium hydroxide and not more than 1% by weight of propionic acid, the calcium propionate and calcium hydroxide each being partly in solution and partly present as solids, the water introduced and that formed during the neutralization is removed as vapor, and, after the calcium hydroxide has been reacted completely, the calcium propionate is separated off and dried.

3. A process as claimed in claim 1, wherein the vaporous mixture, which is at from 90° to 165° C., is compressed to a pressure of from 2 to 20 bar and is passed into an aqueous mixture, at from 120° to 210° C., containing from 27 to 80% by weight of dissolved calcium propionate, from 0.5 to 5% by weight of calcium hydroxide and not more than 1% by weight of propionic acid, the calcium hydroxide being partly in solution and partly present as a solid, the resulting solution is filtered at from 120° to 210° C., the filtrate is cooled to 30°–80° C. and the calcium propionate which has precipitated out is separated off and dried.

4. A process as claimed in claim 1, wherein the azeotrope evaporated off from a continuously operated reactor for the preparation of calcium propionate from calcium hydroxide and propionic acid is used as the vaporous mixture of propionic acid and water.

* * * * *